United States Patent
Koo (10) Patent No.: US 7,998,391 B1
(45) Date of Patent: Aug. 16, 2011

(54) METHOD OF FABRICATING AN ANTINOISE EARPLUG

(76) Inventor: Ja Heon Koo, Busan (KR)

( * ) Notice: Subject to any disclaimer, the term of this patent is extended or adjusted under 35 U.S.C. 154(b) by 0 days.

(21) Appl. No.: 12/758,861

(22) Filed: Apr. 13, 2010

(30) Foreign Application Priority Data

Mar. 15, 2010 (KR) .......................... 10-2010-0022676

(51) Int. Cl.
*B29C 45/14* (2006.01)
*B29C 45/16* (2006.01)
*B29C 70/78* (2006.01)

(52) U.S. Cl. ..... 264/255; 264/275; 264/294; 264/328.1; 264/328.7

(58) Field of Classification Search .................. None
See application file for complete search history.

(56) References Cited

U.S. PATENT DOCUMENTS

| | | | |
|---|---|---|---|
| 5,044,463 A * | 9/1991 | Carr .............................. | 181/135 |
| 5,188,123 A * | 2/1993 | Gardner, Jr. .................. | 128/864 |
| 5,792,998 A * | 8/1998 | Gardner et al. ............... | 181/130 |
| 5,799,658 A | 9/1998 | Falco | |
| 6,264,870 B1 * | 7/2001 | Håkansson .................... | 264/255 |
| 7,192,544 B2 * | 3/2007 | Jenkins et al. ................ | 264/46.4 |
| 7,220,372 B2 * | 5/2007 | Woo et al. ..................... | 264/46.7 |
| 7,727,433 B2 * | 6/2010 | Knauer et al. ................. | 264/46.4 |
| 2006/0138691 A1 * | 6/2006 | Knauer et al. ................. | 264/46.4 |

FOREIGN PATENT DOCUMENTS

JP   11514560   12/1999
KR   1020070039832   10/2008

* cited by examiner

*Primary Examiner* — Edmund H. Lee
(74) *Attorney, Agent, or Firm* — Chapin IP Law, LLC

(57) ABSTRACT

A method of fabricating an anti-noise earplug having an inner tip serving as a core and an outer tip coupled to the inner tip to surround the inner tip and inserted into an ear includes the steps of: (a) shaping the inner tip; (b) fixing the inner tip to an upper mold for shaping the outer tip; (c) disposing the upper mold to face a lower mold having a cavity for shaping the outer tip; (d) injecting a resin composition for forming the outer tip into the lower mold; (e) pressing down the upper mold to the lower mold; (f) curing the resin composition to couple the outer tip to the inner tip; and (g) separating the upper mold from the lower mold and then separating the earplug, in which the outer tip is coupled to the inner tip as a body, from the lower mold. In fabricating the earplug, the inner tip and the outer tip can be molded in an in-line process, thereby improving the fabrication efficiency.

5 Claims, 5 Drawing Sheets

METHOD OF FABRICATING AN ANTINOISE EARPLUG

RELATED APPLICATIONS

This application claims priority to and the benefit of Korean Patent Application No. 10-2010-0022676, entitled "NON-ADHESIVE ANTINOISE EARPLUG AND FABRICATION METHOD THEREOF," filed on Mar. 15, 2010, the contents and teachings of which are hereby incorporated by reference in their entirety.

BACKGROUND

1. Field of the Invention

The present invention relates to a non-adhesive anti-noise earplug and a fabrication method thereof, and more particularly, to a technique not using an adhesive to couple an outer tip for blocking a noise and an inner tip for maintaining an earplug structure.

2. Description of the Related Art

In anti-noise earplugs, an inner tip is formed as a core to maintain the overall shape and an outer tip is formed on the inner tip to bring the earplug into contact with an ear, whereby the leakage of noises can be prevented and the feeling of touch and the waterproof property can be improved.

When the bodies of the earplugs are inserted into a user's ears, the inner tips are supported to come in close contact with both ear holes. At this time, the prevention of the leakage of noises and the improvement in the feeling of touch are accomplished by the outer tips having an elastic cover protruding from the inner tip.

However, the outer tip is fabricated independently of the inner tip and is coupled to the inner tip using an adhesive. Accordingly, when the coupling force is small, the outer tip may be easily separated from the inner tip or may be damaged in long-term use. In a predetermined time, noxious adhesive components may cause pains or inflammation in the ears.

To fabricate an earplug using an adhesive method, molding equipment for shaping the inner tip and molding equipment for shaping the outer tip should be provided independently and equipment for coupling the inner tip and the outer tip should be provided. Therefore, the fabrication cost increases and the equipment maintenance cost also increases, thereby deteriorating the productivity and the economical efficiency.

As described above, the past earplugs have a problem in that the wearing of the earplugs for a long time can cause pains in the ears and the human bodies are exposed to the noxious adhesive components. Therefore, molding equipment for mass production of the earplugs cannot be put into practice, which causes an increase in fabrication cost. As a result, there is a problem that the price of the earplug is made to increase.

SUMMARY

An object of the invention is to couple an inner tip and outer tip of an earplug using a non-adhesive method, thereby reducing the harm of adhesive materials on a human body.

An advantage of some aspects of the invention is that it provides an anti-noise earplug having a configuration in which one outer periphery of the inner tip is surrounded with resin compositions, by previously shaping the inner tip, providing a lower mold having a cavity corresponding to the outline of the outer tip and an upper mold serving to cover the lower mold, fixing the inner tip to the upper mold, injecting the resin composition for forming the outer tip into the cavity, and then pressing the upper mold to the lower mold.

Another advantage of some aspects of the invention is that it provides an anti-noise earplug which can be fabricated in an in-line type and in which the inner tip and the outer tip are coupled to form a body without interposing a noxious adhesive between the inner tip and the outer tip.

According to an aspect of the invention, there is provided an method of fabricating an anti-noise earplug having an inner tip serving as a core and an outer tip coupled to the inner tip to surround the inner tip and inserted into an ear, the method including the steps of: (a) shaping the inner tip; (b) fixing the inner tip to an upper mold for shaping the outer tip; (c) disposing the upper mold to face a lower mold having a cavity for shaping the outer tip; (d) injecting a resin composition for forming the outer tip into the lower mold; (e) pressing down the upper mold to the lower mold; (f) curing the resin composition to couple the outer tip to the inner tip; and (g) separating the upper mold from the lower mold and then separating the earplug, in which the outer tip is coupled to the inner tip as a body, from the lower mold.

The inner tip may be formed of one or more materials selected from polyethylene (PE), acrylonitrile butadiene styrene copolymer (ABS), polypropylene (PP), polystyrene (PS), urethane rubber, and rigid polyurethane.

The resin composition for forming the outer tip may be flexible polyurethane. A solution obtained by mixing a first material with viscosity of 300 to 500 cps/40° C. and a second material with viscosity of 500 to 900 cps/40° C. may be used as the flexible polyurethane and the temperature of the solution may be in the range of 48° C. to 52° C. The second material is mixed with the first material at a ratio of 220 to 240 wt % of the second material to 100 wt % of the first material.

The upper mold may be disposed so that the inner tip is coaxial with the cavity, and the inner tip may be fixed to the upper mold so that the inner tip is separated from the cavity in the state where the upper mold is pressed down to the lower mold.

The cream time, which is a time until a reaction is started after the solution is formed by mixture to form the resin composition, from the step of (d) to the step of (f) may be in the range of 18 to 25 seconds, the tack free time, which is a time until the outer surface of a foam loses the viscous force and the adhesive force (until the foam is not attached to a wooden chopstick when the wooden stick is brought into slight contact with the outer surface of the foam) after the solution of the resin composition is formed by mixture, may be in the range of 160 to 240 seconds, and the rise time, which is a time until the foam rises to the maximum after the solution of the resin composition is formed by mixture, may be in the range of 60 to 140 seconds. Here, the free rise density may be in the range of 0.13 to 0.14 g/cc.

The temperature of the upper mold and the lower mold from the step of (e) to the step of (g) may be adjusted in the range of 60° C. to 80° C. and the stripping time of separating the earplug may be in the range of 8 to 15 minutes.

The step of (a) may include the steps of: (a-1) providing an auxiliary molding frame for defining the cavity for shaping the inner tip; (a-2) inserting the auxiliary molding frame into the cavity of the lower mold; (a-3) injecting a resin composition for forming the inner tip into the auxiliary molding frame; (a-4) pressing down the upper mold to the lower mold and then curing the resin composition to form the inner tip; and (a-5) separating the upper mold from the lower mold and then removing the auxiliary molding frame.

According to another aspect of the invention, there is provided a non-adhesive anti-noise earplug fabricated by the above-mentioned method, wherein the inner tip and the outer tip are formed as a body in an in-line process without interposing an adhesive between the inner tip and the outer tip.

According to the above-mentioned configurations, it is possible to minimize the harm on a human body due to the noxious adhesive and to simplify the fabrication process.

Particularly, it is possible to reduce the number of process steps by previously forming the inner tip and providing the inner tip to the outer tip shaping process, and to fabricate the inner tip by only adding the auxiliary molding frame to the mold for shaping the outer tip, thereby reducing the fabrication cost and the maintenance cost.

In addition, it is possible to strongly couple the outer tip to the inner tip without using an adhesive, by adjusting combination conditions and shaping conditions of the resin composition for forming the outer tip. Accordingly, it is possible to reduce the fabrication cost of the anti-noise earplug and to improve the production efficiency.

DESCRIPTION OF EXEMPLARY
EMBODIMENTS

Hereinafter, an embodiment of the invention will be described in detail with reference to the accompanying drawings.

Advantages and features of the invention and methods for putting them into practice will be apparent from the following embodiments and drawings. However, the invention is not limited to the embodiments, but can be modified in various forms. The embodiments are provided to complete the disclosure of the invention and to completely notify the scope of the invention to those skilled in the art. Like reference numerals in the drawings reference like elements.

Figure 1:
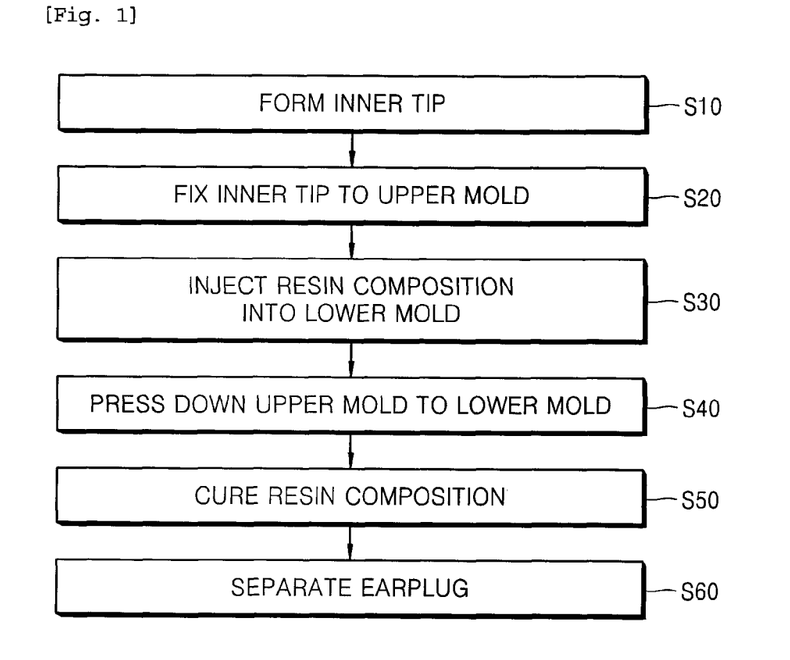
FIG. 1 is a flowchart illustrating a flow of processes of a method of fabricating a non-adhesive anti-noise earplug according to an embodiment of the invention.

FIG. 1 is a flowchart illustrating a flow of processes of a method of fabricating a non-adhesive anti-noise earplug according to an embodiment of the invention.

Referring to FIG. 1, first a step of forming an inner tip (S10) is performed. Here, the inner tip serves as a core forming a skeleton of an earplug and is formed of one or more materials selected from polyethylene (PE), acrylonitrile butadiene styrene copolymer (ABS), polypropylene (PP), polystyrene (PS), urethane rubber, and rigid polyurethane.

In the embodiment, the inner tip should be coupled to an outer tip formed of flexible polyurethane. Accordingly, when rigid polyurethane is used as the inner tip, it is possible to obtain a more excellent coupling effect. The curing time of rigid polyurethane is preferably in the range of 3 to 6 minutes, whereby the inner tip can have satisfactory strength as a core and can enhance the elasticity and the coupling force to other resin materials. When the curing time is less than 3 minutes, the inner tip cannot have satisfactory strength. When the curing time is greater than 6 minutes, the elasticity and the coupling force may decrease.

Then, a step of fixing one end of the inner tip to an upper mold for forming an outer tip (S20) is performed. This step is performed to couple the outer tip to the inner tip at the same time as forming the outer tip by inserting the inner tip into a cavity of a lower mold for defining the shape of the outer tip in a mold pressing step of forming the outer tip.

Then, a step of injecting a resin composition for forming the outer tip into the cavity of the lower mold (S30) is performed. Here, flexible polyurethane is used as the resin composition. Here, a solution obtained by mixing a first material with viscosity of 300 to 500 cps/40° C. and a second material with viscosity of 500 to 900 cps/40° C. is preferably used to form the outer tip.

Here, the temperature of the solution is in the range of 48° C. to 52° C. In the mixture ratio, 220 to 240 wt % of the second material is mixed with 100 wt % of the first material.

When the second material having the higher viscosity is not mixed by 200 wt % or more, the hardness suitable for the outer tip of the earplug cannot be obtained. When the second material is mixed to be greater than 240 wt %, the hardness is excessively great to make it difficult to insert the outer tip into an ear hole, thereby deteriorating the feeling of touch.

Then, a step of pressing down the upper mold, to which the inner tip is fixed, to the lower mold (S40) is performed. Here, the inner tip is immersed in the resin composition filled in the cavity so as to surround one end of the inner tip with the resin composition.

Accordingly, before the upper mold is pressed down, the upper mold should be disposed so that the inner tip is coaxial with the cavity, and the inner tip should be fixed to the upper mold so that the inner tip is separated by a predetermined gap from the cavity in the state where the upper mold is pressed down to the lower mold. At this time, the separation gap is the thickness of the outer tip. The outer tip shaped in this way is inserted into an ear and serves to block noises.

A step of curing the resin composition in the state where the upper mold is pressed down to the lower mold (S50) is then performed.

Here, the curing temperature of the upper mold and the lower mold is preferably adjusted in the range of 60° C. to 80° C.

The cream time, which is a time until a reaction for forming the resin composition is started after the solution is formed by mixture, in the above-mentioned steps is adjusted preferably in the range of 18 to 25 seconds. The tack free time, which is a time until the outer surface of a foam loses the viscous force and the adhesive force (until the foam is not attached to a wooden chopstick when the wooden stick is brought into slight contact with the outer surface of the foam) after the solution of the resin composition is formed by mixture, is preferably in the range of 160 to 240 seconds. The rise time, which is a time until the foam rises to the maximum after the solution of the resin composition is formed by mixture, is preferably in the range of 60 to 140 seconds. Here, the free rise density is in the range of 0.13 to 0.14 g/cc.

A step of separating the formed earplug from the lower mold (S60) is then performed.

Here, it is preferable that the steps until finally curing and separating the earplug after forming the solution of the resin composition should be performed in the range of 8 to 15 minutes and the molding temperature should be adjusted in the range of 60° C. to 80° C.

The cream time, the tack free time, the rise time, and the stripping time are in the above-mentioned ranged. When the processes are performed to be shorter than the minimum time of the respective ranges or the molding is performed at a temperature less than 60° C., the outer tip of the earplug may not have a proper shape. When the processes are performed to be greater than the maximum time of the respective ranges or the molding temperature is greater than 80° C., the resin composition is deteriorated not to form a normal outer tip and the characteristic thereof is markedly lowered.

As described above, since the method of fabricating an anti-noise earplug according to the embodiment of the invention employs the method of coupling the inner tip to the outer tip while performing the molding process of curing the outer tip formed of flexible polyurethane, instead of forming the outer tip as an anti-noise member in a separate process and coupling the outer tip to the inner tip, it is possible to solve the problems with body contamination and durability, which are generated in using the existing noxious adhesive.

The method of fabricating a non-adhesive anti-noise earplug according to the invention will be described below with reference to specific examples for coupling the inner tip to the outer tip.

FIGS. 2 to 6 are sectional views illustrating a non-adhesive anti-noise earplug and a fabrication method thereof according to an embodiment of the invention.

Figure 2:
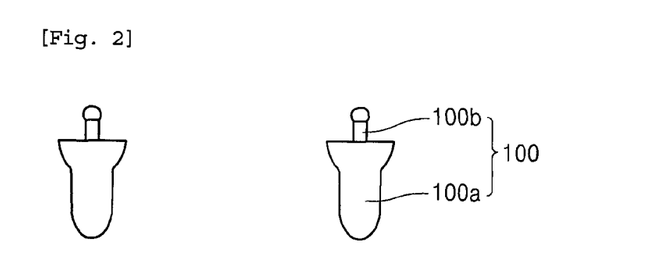
FIGS. 2 to 6 are sectional views illustrating a non-adhesive anti-noise earplug and a fabrication method thereof according to an embodiment of the invention.

Referring to FIG. 2, an inner tip 100 including a knob 100b of the inner tip and a core 100a of the inner tip as an inner core is molded. Here, the shape of the inner tip 100 is not limited to the drawing, but may be a simple cylinder. Accordingly, the shape is not particularly limited as long as it can be easily inserted into an ear.

Figure 7:
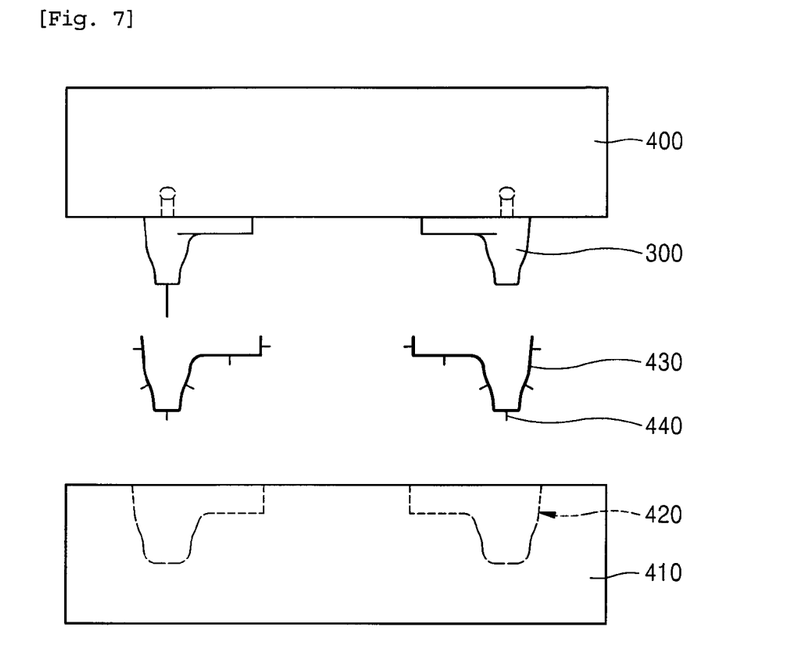
FIGS. 7 to 10 are sectional views illustrating a non-adhesive anti-noise earplug and a fabrication method thereof according to another embodiment of the invention.

In the drawing, the inner tip 100 is formed using a particular inner tip mold, but may be formed using an outer tip mold as shown in FIG. 7.

In this case, since the number of molds can be reduced in comparison with the existing fabrication equipment, it is possible to reduce the equipment cost and the maintenance cost. Here, even when a separate mold is used to form the inner tip 100, the inner tip 100 should be fixed to the upper mold for molding the outer tip. Accordingly, the upper mold for forming the inner tip and the upper mold for forming the outer tip should be shared.

Therefore, the number of molds can be reduced similarly.

Since the formed inner tip can be transported right to the mold for forming the outer tip, the overall processes of fabricating an earplug can be designed in an in-line process.

While components might be contaminated or damaged in the course of forming and transporting the components in the past, such problems with defective products can be solved using the above-mentioned in-line equipment and the process time can be reduced, thereby improving the productivity.

Figure 3:
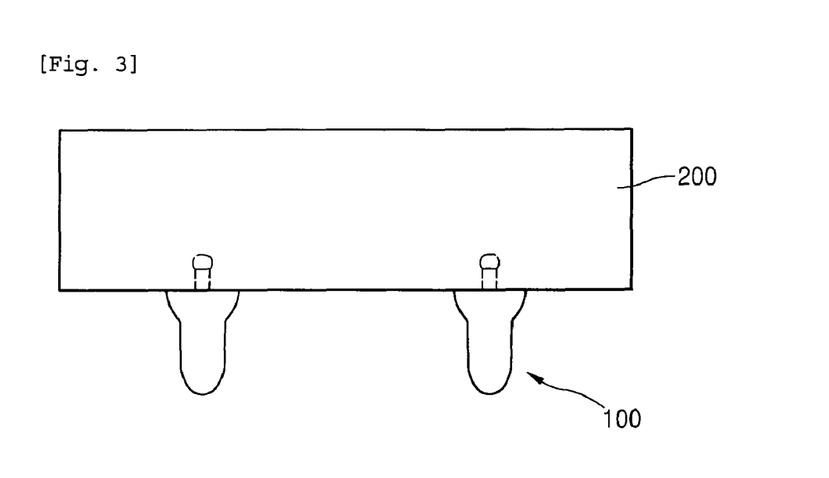

Then, as shown in FIG. 3, the inner tip 100 is fixed to the upper mold 200 for forming the outer tip.

Here, the inner tip 100 should be disposed so that the virtual center line of the inner tip 100 is equal to the virtual center line of the cavity, and the upper mold for forming the inner tip 100 can be used as the upper mold 200 for forming the outer tip.

Therefore, a particular protrusion may be further formed in the knob of the inner tip 100 so that the inner tip can be easily separated from the upper mold for forming the inner tip and can be left in the upper mold without being separated therefrom, after the inner tip 100 is cured.

Figure 4:
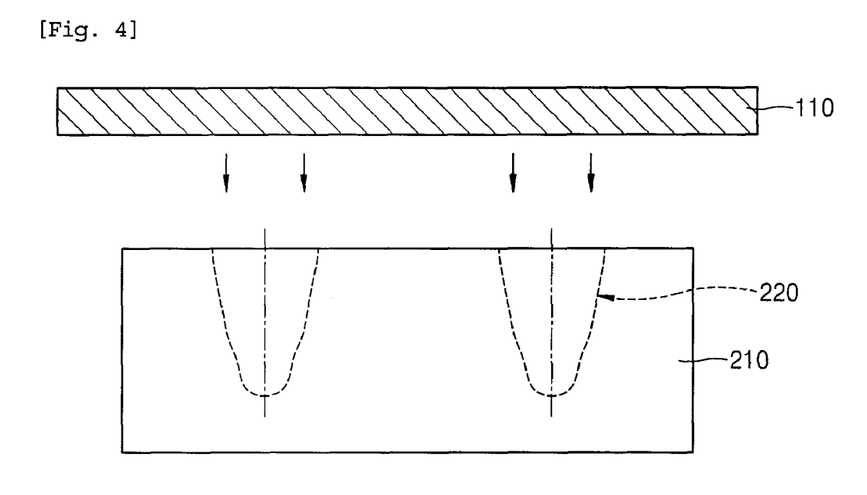

Then, as shown in FIG. 4, the resin composition 110 for forming the outer tip is injected into the cavity 220 of the lower mold 210. At this time, it is preferable that the resin composition 110 should be filled in the cavity up to 80% to 100% of the height of the cavity 220.

When the resin composition is injected to be lower than 80%, the outer tip may not have a complete shape. When the resin composition is injected to higher than 100%, the injected resin composition flows over the surface of the mold and the resin composition overflowing from the cavity can serve as a contamination source of the mold.

Figure 5:
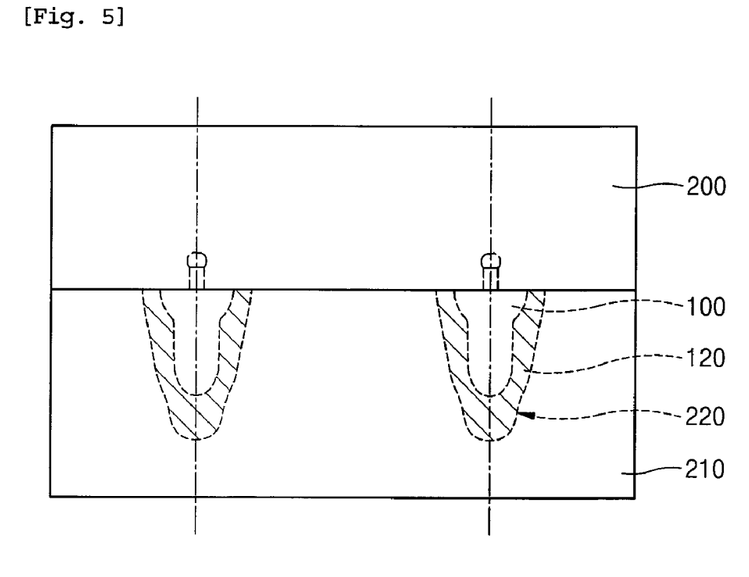

Then, as shown in FIG. 5, the upper mold 200 is pressed down to the lower mold 210 to form the shape of the outer tip 120 with the inner tip 100 fixed to the upper mold 200.

Here, the outer tip is naturally coupled to the inner tip 100.

Since the coupling force increases by curing the resin composition of the outer tip 120, it is possible to fabricate an earplug having a coupling force stronger than that of the existing earplug fabricated using an adhesive.

Figure 6:
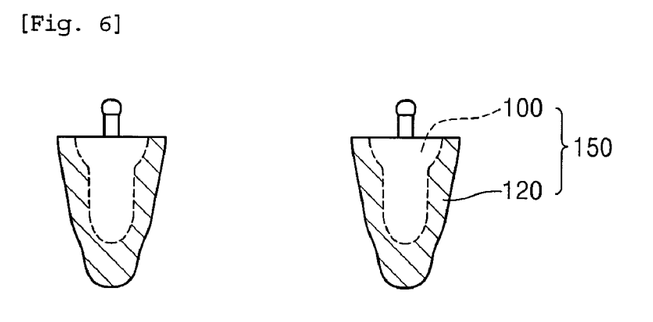

The earplug 150 having the outer tip 120 coupled to the inner tip 100 is separated from the lower mold 210 and the upper mold 200, whereby the fabrication processes are finished.

In the above-mentioned embodiment, the method of fabricating a non-adhesive anti-noise earplug is embodied by fixing the inner tip to a mold for forming the outer tip after forming the inner tip. Accordingly, since the earplug does not contain an adhesive which is a noxious chemical, it is not harmless to a human body. Therefore, it is possible to prevent the generation of the inflammation or the like.

Since the upper mold for forming the inner tip is not necessary and the in-line process can be implemented, it is possible to simplify the fabrication process.

Here, a method of fabricating a non-adhesive anti-noise earplug according to another embodiment of the invention allows the mold for forming the inner tip and the mold for forming the outer tip to be shared. In this configuration, the equipment cost and the maintenance cost can be reduced, thereby improving the productivity. The details thereof will be described below.

FIGS. 7 to 10 are sectional views illustrating a non-adhesive anti-noise earplug and a fabrication method thereof according to another embodiment of the invention.

As shown in FIG. 7, an inner tip 300 and an other tip can be formed using a single mold by using an upper mold 400 and a lower mold 410 for forming the outer tip and inserting an auxiliary molding frame 430 for defining a cavity for forming the inner tip into a cavity 420 for forming the outer tip.

At this time, the auxiliary molding frame 430 may have various shapes, and the auxiliary molding frame 430 having the shape of the outer tip can be provided. As shown in the drawing, the auxiliary molding frame has a thin film shape and spacers 440 corresponding to the thickness of the outer tip can be coupled to the outer surface thereof.

The auxiliary molding frame 430 may be of a one-bodied type or a division type which can be divided into two parts.

The auxiliary molding frame 430 can be reused repeatedly in such a way that it is separated from the mold after the inner tip 300 is formed, and it is inserted again into the cavity for forming the outer tip after the subsequent outer tip molding step is finished.

Figure 8:
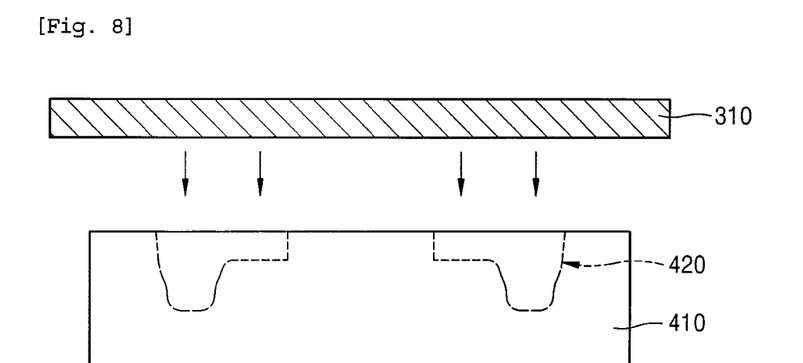

Then, as shown in FIG. 8, a resin composition 310 for forming the outer tip is injected into the cavity 420 for forming the outer tip in the state where the auxiliary molding frame 430 is removed.

Figure 9:
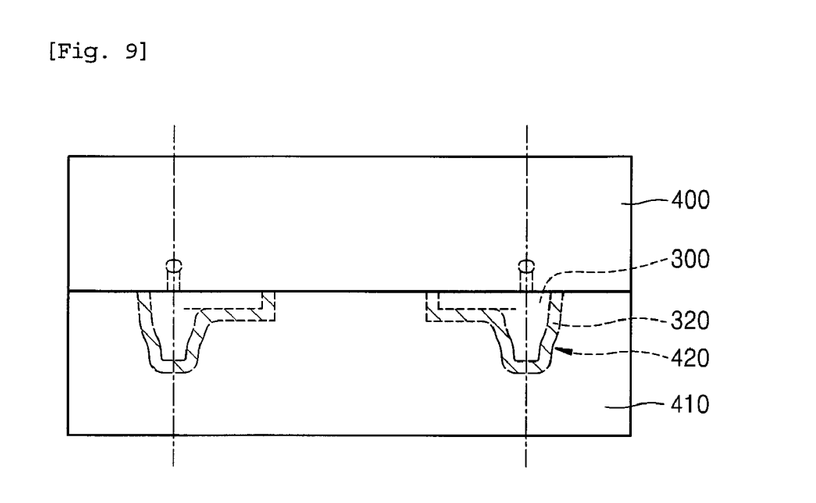

As shown in FIG. 9, the upper mold 400 is pressed down to insert the inner tip 300 into the cavity 420 of the lower mold 410, so that the outer tip 320 is formed in a space corresponding to the separation gap between the inner tip 300 and the cavity 420.

By performing the curing step, the coupling force between the inner tip 300 and the outer tip 320 is increased.

Figure 10:
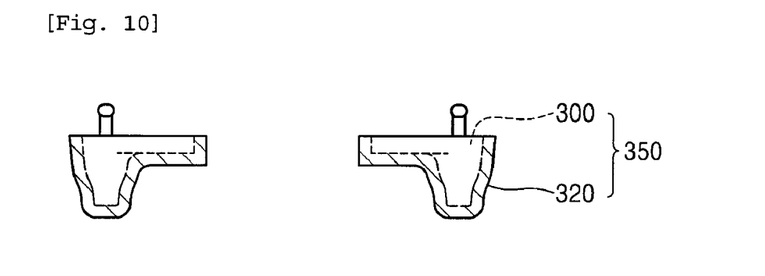

Then, as shown in FIG. 10, the upper mold 400 and the lower mold 410 are removed. In this way, the earplug 350 having the outer tip 320 coupled to the inner tip 300 is fabricated in a non-adhesive method.

In the above-mentioned embodiment, since the method for reducing the equipment cost is added to the method of fabricating a non-adhesive anti-noise earplug, it is possible to further improve the equipment cost and the fabrication efficiency.

Figure 11:
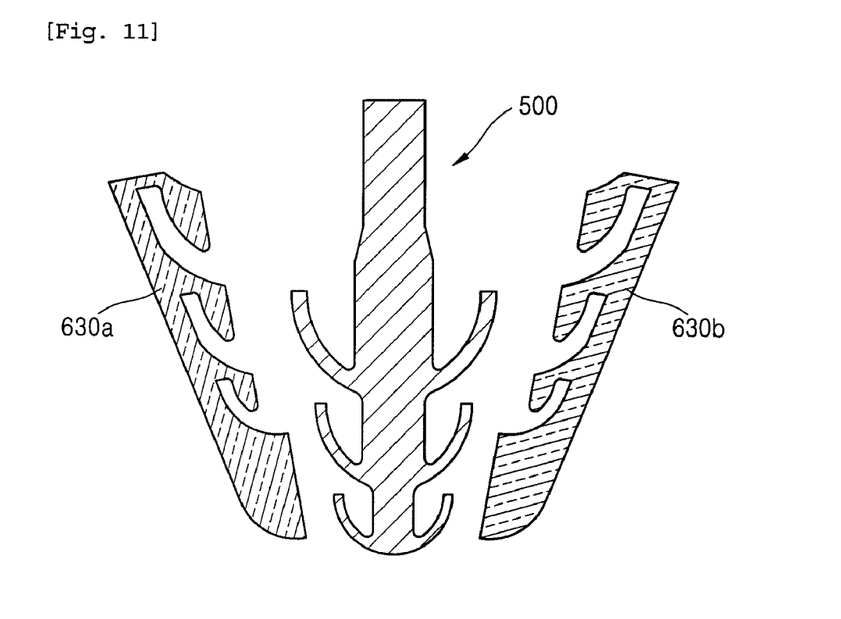
FIG. 11 is a sectional view illustrating another example of an auxiliary molding frame shown in FIG. 7.

The auxiliary molding frame shown in FIG. 7 plays a core role in the above-mentioned embodiment. FIG. 11 is an example of the auxiliary molding frame.

As shown in FIG. 11, when plural blades for improving the coupling force are formed in an inner tip 500, auxiliary molding frames having cavities corresponding to the respective blades are necessary.

In this case, when a one-bodied auxiliary molding frame is used, the auxiliary molding frame may not be easily pull down and removed due to the blades.

Therefore, the auxiliary molding frame can be formed to be divided into several parts. In the drawing, after the inner tip 500 having the outer blades is formed, the auxiliary molding frame can be divided into a first auxiliary molding frame 630a and a second auxiliary molding frame 630b and can be easily removed.

According to the above-mentioned embodiments of the invention, by coupling the inner tip and the outer tip of the anti-noise earplug in a non-adhesive way, it is possible to minimize the damage on a human body due to a noxious adhesive component and to simplify the fabrication process.

Particularly, the invention can be applied to earplugs used in hiking or leisure sports other than the anti-noise earplug, and can be modified in various forms such as a string-coupling type by simply changing the inner tip.

The application fields of the invention can be easily extended up to the fields of hearing aid applications and earphone tips for listening to music.

While the invention has been described with reference to the finite embodiments and drawings, the invention is not limited to the embodiments, but it will be understood by those skilled in the art that the invention can be modified in various forms without departing from the technical spirit of the invention taught from the appended claims. Therefore, the technical spirit of the invention should be read from only the appended claims and the equivalent modifications thereof should belong to the spirit and scope of the invention.

What is claimed is:

1. A method of fabricating an anti-noise earplug having an inner tip serving as a core and an outer tip coupled to the inner tip to surround the inner tip and inserted into an ear, the method comprising the steps of:
   (a) shaping the inner tip;
   (b) fixing the inner tip to an upper mold for shaping the outer tip;
   (c) disposing the upper mold to face a lower mold having a cavity for shaping the outer tip, wherein the upper mold is disposed so that the inner tip is coaxial with the cavity for shaping the outer tip, and the inner tip is fixed to the upper mold so that the inner tip is separated from the cavity for shaping the outer tip in the state where the upper mold is pressed down to the lower mold;
   (d) injecting a resin composition for forming the outer tip into the lower mold;
   (e) pressing down the disposed upper mold having the inner tip fixed thereto to the lower mold having the injected resin composition therein;
   (f) curing the infected resin composition for forming the outer tip to couple the outer tip to the inner tip; and
   (g) separating the upper mold from the cured resin composition in the lower mold and then separating the earplug, in which the outer tip is coupled to the inner tip as a body, from the lower mold;
   wherein shaping the inner tip comprises:
      providing an auxiliary molding frame for defining a cavity for shaping the inner tip;
      inserting the auxiliary molding frame into the cavity for shaping the outer tip;
      injecting a resin composition for forming the inner tip into the auxiliary molding frame inserted into the cavity for shaping the outer tip;
      pressing down the upper mold for shaping the outer tip to the lower mold and then curing the injected resin composition to form the inner tip; and
   separating the upper mold from the lower mold and then removing the auxiliary molding frame from the cured injected resin forming the inner tip;
   wherein the inner tip is formed of one or more materials selected from polyethylene (PE), acrylonitrile butadiene styrene copolymer (ABS), polypropylene (PP), polystyrene (PS), urethane rubber, and rigid polyurethane;
   wherein the resin composition for forming the outer tip is flexible polyurethane;
   wherein a solution obtained by mixing a first material with viscosity of 300 to 500 cps/40° C. and a second material with viscosity of 500 to 900 cps/40° C. is used as the flexible polyurethane and the temperature of the solution is in the range of 48° C. to 52° C.;
   wherein the second material is mixed with the first material at a ratio of 220 to 240 wt % of the second material to 100 wt % of the first material.

2. The method according to claim 1, wherein the cream time of shaping the resin composition from the step of (d) to the step of (f) is in the range of 18 to 25 seconds, the tack free time is in the range of 160 to 240 seconds, the rise time is in the range of 60 to 140 seconds, and the free rise density is in the range of 0.13 to 0.14 g/cc.

3. The method according to claim 1, wherein the temperature of the upper mold and the lower mold from the step of (e) to the step of (g) is adjusted in the range of 60° C. to 80° C. and the stripping time of separating the earplug is in the range of 8 to 15 minutes.

4. A method of fabricating an anti-noise earplug having an inner tip serving as a core and an outer tip coupled to the inner tip to surround the inner tip and inserted into an ear, the method comprising the steps of:
   (a) shaping the inner tip;
   (b) fixing the inner tip to an upper mold for shaping the outer tip;
   (c) disposing the upper mold to face a lower mold having a cavity for shaping the outer tip, wherein the upper mold is disposed so that the inner tip is coaxial with the cavity for shaping the outer tip, and the inner tip is fixed to the upper mold so that the inner tip is separated from the cavity for shaping the outer tip in the state where the upper mold is pressed down to the lower mold;
   (d) injecting a resin composition for forming the outer tip into the lower mold;
   (e) pressing down the disposed upper mold having the outer tip fixed thereto to the lower mold having the injected resin composition therein;
   (f) curing the infected resin composition to couple the outer tip to the inner tip; and (g) separating the upper mold from the cured resin composition in the lower mold and then separating the earplug, in which the outer tip is coupled to the inner tip as a body, from the lower mold;

wherein a cream time of shaping the resin composition from the step of (d) to the step of (f) is in the range of 18 to 25 seconds, the tack free time is in the range of 160 to 240 seconds, the rise time is in the range of 60 to 140 seconds, and the free rise density is in the range of 0.13 to 0.14 g/cc.

5. The method according to claim 4, wherein a temperature of the upper mold and the lower mold from the step of (e) to the step of (g) is adjusted in the range of 60° C. to 80° C. and the stripping time of separating the earplug is in the range of 8 to 15 minutes.

\* \* \* \* \*